United States Patent
Turgeman et al.

(10) Patent No.: US 12,011,237 B2
(45) Date of Patent: Jun. 18, 2024

(54) SYSTEM AND METHOD OF GESTURE DETECTION AND DEVICE POSITIONING

(71) Applicant: Mazor Robotics Ltd., Caesarea (IL)

(72) Inventors: Avi Turgeman, Beer Yaakov (IL); Yonatan Ushpizin, Glil Yam (IL); Eli Zehavi, Tel Aviv (IL); Ido Zucker, Tel Aviv (IL)

(73) Assignee: Mazor Robotics Ltd., Caesarea (IL)

( * ) Notice: Subject to any disclaimer, the term of this patent is extended or adjusted under 35 U.S.C. 154(b) by 479 days.

(21) Appl. No.: 17/331,081

(22) Filed: May 26, 2021

(65) Prior Publication Data
US 2022/0378521 A1    Dec. 1, 2022

(51) Int. Cl.
A61B 34/30    (2016.01)
A61B 17/86    (2006.01)
A61B 34/00    (2016.01)
G06F 3/01    (2006.01)
G06T 7/50    (2017.01)

(52) U.S. Cl.
CPC .............. *A61B 34/30* (2016.02); *A61B 17/86* (2013.01); *A61B 34/25* (2016.02); *G06F 3/017* (2013.01); *G06T 7/50* (2017.01); *A61B 2034/743* (2016.02); *A61B 2034/744* (2016.02); *G06T 2207/10028* (2013.01); *G06T 2207/30012* (2013.01)

(58) Field of Classification Search
CPC ......... A61B 34/30; A61B 17/86; A61B 34/25; G06F 3/017; G06T 7/50; G06T 2207/10028; G06T 2207/30012
See application file for complete search history.

(56) References Cited

U.S. PATENT DOCUMENTS

| | | | |
|---|---|---|---|
| 10,786,327 B2 | 9/2020 | Anderson et al. | |
| 2011/0060423 A1 | 3/2011 | Bonfiglio et al. | |
| 2012/0249977 A1 | 10/2012 | Abri et al. | |
| 2013/0225999 A1 | 8/2013 | Banjanin et al. | |
| 2014/0336669 A1* | 11/2014 | Park | A61B 34/30 606/130 |
| 2015/0100066 A1* | 4/2015 | Kostrzewski | A61B 34/30 606/130 |
| 2015/0253865 A1 | 9/2015 | Hayashi et al. | |
| 2016/0278864 A1 | 9/2016 | Paitel | |
| 2018/0368656 A1* | 12/2018 | Austin | A61B 1/045 |
| 2019/0290374 A1* | 9/2019 | Ramadorai | A61B 34/30 |
| 2019/0380791 A1* | 12/2019 | Fuerst | G06F 3/0346 |
| 2022/0061921 A1* | 3/2022 | Crawford | A61B 34/20 |

OTHER PUBLICATIONS

International Search Report and Written Opinion for International (PCT) Patent Application No. PCT/IL2022/050529, dated Nov. 18, 2022, 20 pages.
Invitation to Pay Additional Fees for International (PCT) Patent Application No. PCT/IL2022/050529, dated Sep. 26, 2022, 11 pages.

* cited by examiner

*Primary Examiner* — Kira Nguyen
(74) *Attorney, Agent, or Firm* — Sheridan Ross P.C.

(57) ABSTRACT

A system according to at least one embodiment of the present disclosure includes an imaging source; an imaging detector; a depth sensor; and a controller, where the controller receives image information from the depth sensor, determines a gesture in relation to a working volume, and moves the imaging source and the imaging detector relative to the working volume based on the gesture.

20 Claims, 5 Drawing Sheets

SYSTEM AND METHOD OF GESTURE DETECTION AND DEVICE POSITIONING

FIELD

The present technology generally relates to surgical procedures, and more particularly to utilizing gesture input to assist with surgical procedures.

BACKGROUND

Surgical robots may assist a surgeon or other medical provider in carrying out a surgical procedure or may complete one or more surgical procedures autonomously. Imaging may be used by a medical provider for diagnostic and/or therapeutic purposes. Imaging may be used to capture images of patient anatomy while carrying out a surgery or surgical procedure. The captured images may be used to guide or navigate a surgical robot.

SUMMARY

Example aspects of the present disclosure include:

A system according to at least one embodiment of the present disclosure comprises: an imaging source; an imaging detector; a depth sensor; and a controller, wherein the controller receives image information from the depth sensor, determines a gesture in relation to a working volume, and moves the imaging source and the imaging detector relative to the working volume based on the gesture.

Any of the aspects herein, wherein the gesture is performed by a surgeon.

Any of the aspects herein, wherein the gesture comprises a hand gesture.

Any of the aspects herein, wherein the controller determines the gesture based on a silhouette formed on an anatomical element by the gesture.

Any of the aspects herein, wherein the controller determines a direction associated with the gesture and causes the imaging source and imaging detector to move in relation to the direction.

Any of the aspects herein, wherein the imaging source is moved with a first robotic arm and wherein the imaging detector is moved with a second robotic arm.

Any of the aspects herein, wherein the controller causes the imaging source and the imaging detector to capture an image of an anatomical object in the working volume, and wherein the controller causes the image to be rendered to a user interface.

Any of the aspects herein, wherein the anatomical object is a vertebra.

Any of the aspects herein, wherein the anatomical object is a rib.

A system according to at least one embodiment of the present disclosure comprises: a processor; and a memory storing data for processing by the processor that, when processed by the processor, cause the processor to: receive image information from a depth sensor; determine a gesture in relation to a working volume; cause an imaging source and an imaging detector to move relative to the working volume based on the gesture; and cause an image of an anatomical object in the working volume to be captured.

Any of the aspects herein, wherein the gesture is performed by an individual in an operating room.

Any of the aspects herein, wherein the gesture is at least one of a hand gesture, an arm gesture, and an eye gesture.

Any of the aspects herein, wherein the processor determines the gesture based on a silhouette formed on the anatomical object by the gesture.

Any of the aspects herein, wherein the data further causes the processor to: cause a surgical tool to move relative to the working volume based on the gesture.

Any of the aspects herein, wherein the anatomical object comprises at least one of a vertebra and a rib.

Any of the aspects herein, wherein the working volume is determined based on a surgical plan.

Any of the aspects herein, wherein the working volume contains a screw, and wherein the data further causes the processor to verify a position of the screw based on the gesture.

Any of the aspects herein, wherein the instructions further cause the processor to:

render, to a user interface, the image of the anatomical object.

A method according to at least one embodiment of the present disclosure comprises: receiving image information from a depth sensor; determining a gesture in relation to a working volume; causing an imaging source and an imaging detector to move relative to the working volume based on the gesture; and causing an image of an anatomical object in the working volume to be captured with the imaging detector.

Any of the aspects herein, further comprising: determining a direction associated with the gesture; and causing the imaging source and the imaging detector to move in relation to the direction associated with the gesture.

Any aspect in combination with any one or more other aspects.

Any one or more of the features disclosed herein.

Any one or more of the features as substantially disclosed herein.

Any one or more of the features as substantially disclosed herein in combination with any one or more other features as substantially disclosed herein.

Any one of the aspects/features/embodiments in combination with any one or more other aspects/features/embodiments.

Use of any one or more of the aspects or features as disclosed herein.

It is to be appreciated that any feature described herein can be claimed in combination with any other feature(s) as described herein, regardless of whether the features come from the same described embodiment.

The details of one or more aspects of the disclosure are set forth in the accompanying drawings and the description below. Other features, objects, and advantages of the techniques described in this disclosure will be apparent from the description and drawings, and from the claims.

The phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together. When each one of A, B, and C in the above expressions refers to an element, such as X, Y, and Z, or class of elements, such as $X_1$-$X_n$, $Y_1$-$Y_m$, and $Z_1$-$Z_o$, the phrase is intended to refer to a single element selected from X, Y, and Z, a combination of elements selected from the same class (e.g., $X_1$ and $X_2$) as well as a combination of elements selected from two or more classes (e.g., $Y_1$ and $Z_o$).

The term "a" or "an" entity refers to one or more of that entity. As such, the terms "a" (or "an"), "one or more" and "at least one" can be used interchangeably herein. It is also to be noted that the terms "comprising", "including", and "having" can be used interchangeably.

The preceding is a simplified summary of the disclosure to provide an understanding of some aspects of the disclosure. This summary is neither an extensive nor exhaustive overview of the disclosure and its various aspects, embodiments, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and configurations of the disclosure are possible utilizing, alone or in combination, one or more of the features set forth above or described in detail below.

Numerous additional features and advantages of the present invention will become apparent to those skilled in the art upon consideration of the embodiment descriptions provided hereinbelow.

BRIEF DESCRIPTION OF THE DRAWINGS

The accompanying drawings are incorporated into and form a part of the specification to illustrate several examples of the present disclosure. These drawings, together with the description, explain the principles of the disclosure. The drawings simply illustrate preferred and alternative examples of how the disclosure can be made and used and are not to be construed as limiting the disclosure to only the illustrated and described examples. Further features and advantages will become apparent from the following, more detailed, description of the various aspects, embodiments, and configurations of the disclosure, as illustrated by the drawings referenced below.

DETAILED DESCRIPTION

Figure 1A:
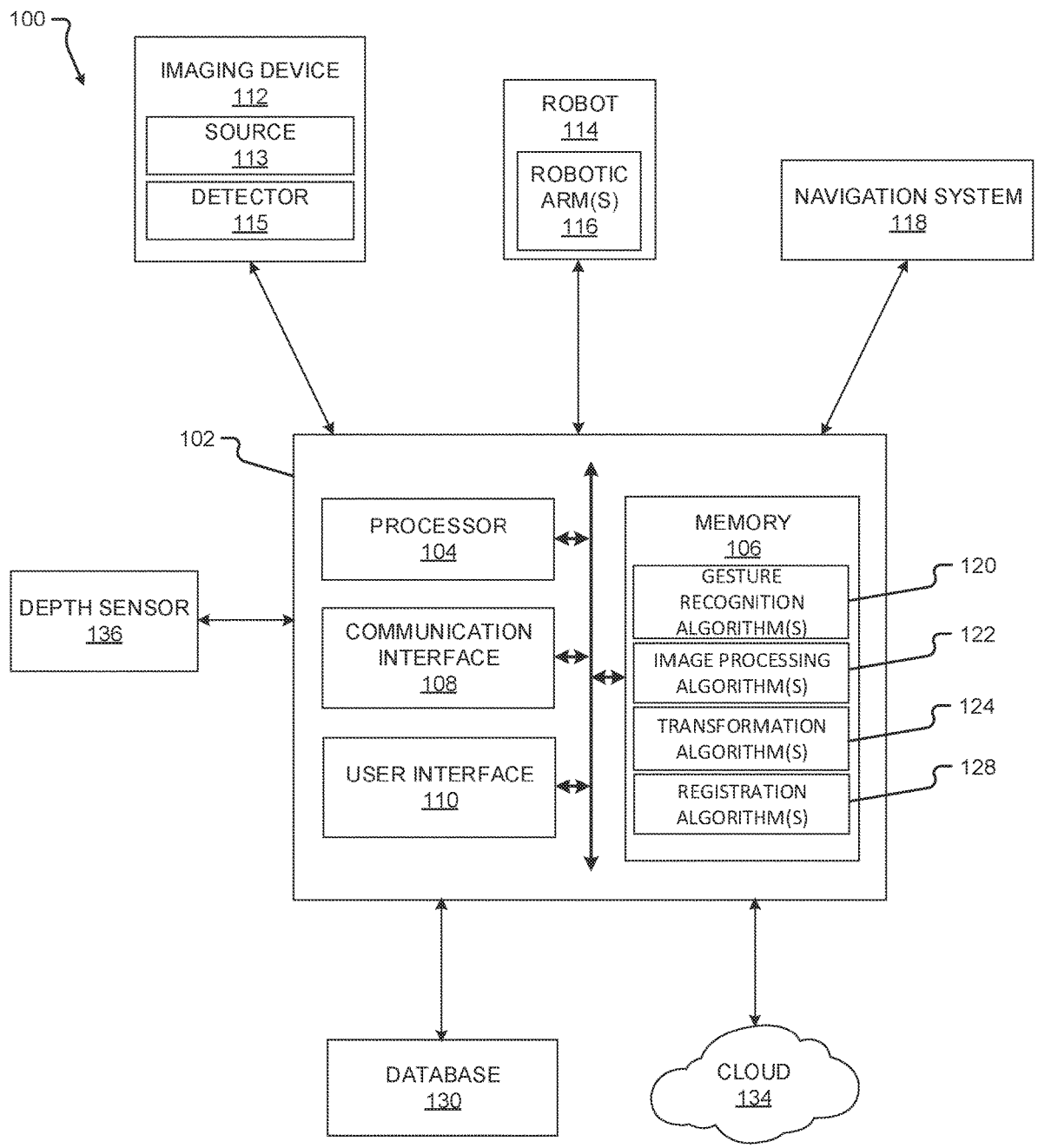
FIG. 1A is a block diagram of a system implementing gesture-based navigation and control according to at least one embodiment of the present disclosure.

It should be understood that various aspects disclosed herein may be combined in different combinations than the combinations specifically presented in the description and accompanying drawings. It should also be understood that, depending on the example or embodiment, certain acts or events of any of the processes or methods described herein may be performed in a different sequence, and/or may be added, merged, or left out altogether (e.g., all described acts or events may not be necessary to carry out the disclosed techniques according to different embodiments of the present disclosure). In addition, while certain aspects of this disclosure are described as being performed by a single module or unit for purposes of clarity, it should be understood that the techniques of this disclosure may be performed by a combination of units or modules associated with, for example, a computing device and/or a medical device.

In one or more examples, the described methods, processes, and techniques may be implemented in hardware, software, firmware, artificial neural networks, or any combination thereof. If implemented in software, the functions may be stored as one or more instructions or code on a computer-readable medium and executed by a hardware-based processing unit. If implemented in an artificial neural network, the data (e.g., a model data file, combinations of model data files, etc.) may be stored on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions, model data files, may be executed by one or more processors, such as one or more digital signal processors (DSPs), general purpose microprocessors (e.g., Intel Core i3, i5, i7, or i9 processors; Intel Celeron processors; Intel Xeon processors; Intel Pentium processors; AMD Ryzen processors; AMD Athlon processors; AMD Phenom processors; Apple A10 or 10X Fusion processors; Apple A11, A12, A12X, A12Z, or A13 Bionic processors; or any other general purpose microprocessors), graphics processing units (e.g., Nvidia GeForce RTX 2000-series processors, Nvidia GeForce RTX 3000-series processors, AMD Radeon RX 5000-series processors, AMD Radeon RX 6000-series processors, or any other graphics processing units), application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

Before any embodiments of the disclosure are explained in detail, it is to be understood that the disclosure is not limited in its application to the details of construction and the arrangement of components set forth in the following description or illustrated in the drawings. The disclosure is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Further, the present disclosure may use examples to illustrate one or more aspects thereof. Unless explicitly stated otherwise, the use or listing of one or more examples (which may be denoted by "for example," "by way of example," "e.g.," "such as," or similar language) is not intended to and does not limit the scope of the present disclosure.

The terms proximal and distal are used in this disclosure with their conventional medical meanings, proximal being closer to the operator or user of the system, and further from the region of surgical interest in or on the patient, and distal being closer to the region of surgical interest in or on the patient, and further from the operator or user of the system.

Using intraoperative x-ray imaging (e.g., using a C-arm or an O-arm) sometimes requires determining the position and orientation of certain devices (e.g., an imaging source, an imaging detector, etc.) in the system. The determination can be time-intensive and inaccuracies in the positioning and orientation of the devices can result in the imaging process needing to be repeated. Repetition of the imaging process can result in an unnecessary and dangerous increase in the amount of time dedicated to the surgical process.

According to at least one embodiment of the present disclosure, the above issues may be resolved by using systems, methods, and/or algorithms described herein where, by pointing to a certain area, robotic arms are moved to the location in space to capture one or more images or image information. One robotic arm may carry or move an imaging source, while a second robotic arm may carry or move an imaging detector. The imaging source and imaging detector may then capture 2D or 3D images of the area. Systems and methods described herein may comprise a depth camera or sensor for skeleton interpretation, one or more robotic arms, an imaging detector, and an imaging source. In at least one embodiment, a system or method may be performed during spinal procedures that implement the use of x-rays (e.g., spinal reconstruction, spinal surgery planning, intraoperative spinal surgery, etc.), surgeries or surgical procedures that include screw placement (e.g., spinal fusion), and/or surgeries or surgical procedures that utilize or implement robotic guidance systems (e.g., autonomous or semi-autonomous surgeries or surgical procedures).

Embodiments of the present disclosure may implement region of interest pointing, such that gestures (e.g., hand gestures) are used as commands to move one or more surgical components without requiring the use of predefined locations and/or human interface control.

Embodiments of the present disclosure provide technical solutions to: (1) long operating room and/or surgery time; (2) extensive x-ray exposure; and/or (3) complex surgeries requiring multiple surgeons and/or technicians. Embodiments of the present disclosure beneficially reduce operating times, reduce x-ray exposure to the patient and/or the surgeon, and reduce the number of medical personnel required for procedures (e.g., the surgeon may solely operate the gesture-based systems and methods discussed herein).

Figure 1B:
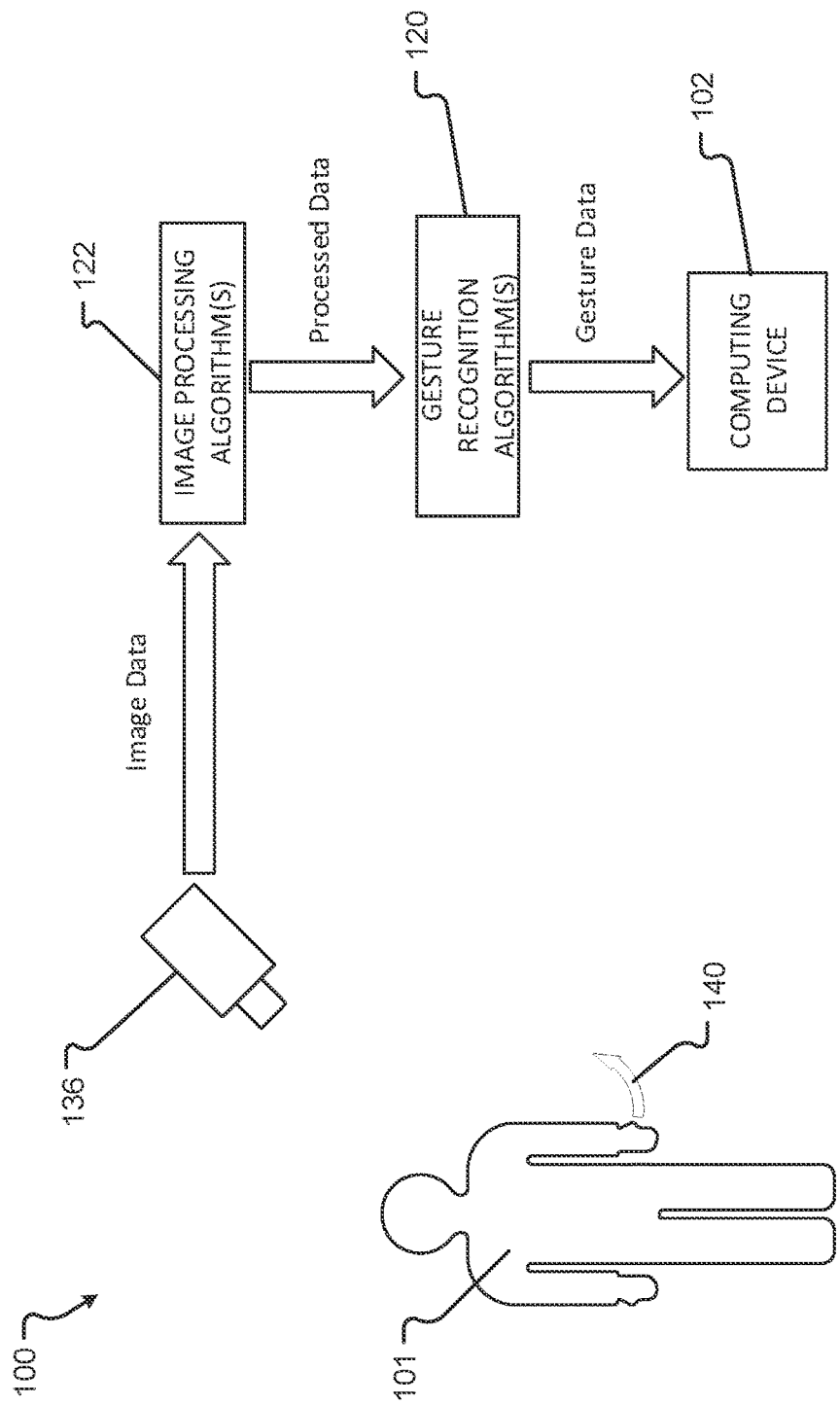
FIG. 1B is a block diagram of the system capturing and processing a captured gesture according to at least one embodiment of the present disclosure.

Turning first to FIGS. 1A-1B, aspects of a system 100 according to at least one embodiment of the present disclosure is shown. The system 100 may be used to cause images of a working volume to be captured based on one or more gestures, to cause imaging elements to be moved relative to a working volume based on one or more gestures, and/or carry out one or more other aspects of one or more of the methods disclosed herein. The system 100 is illustrated to include a computing device 102, one or more imaging devices 112, a robot 114, a navigation system 118, a database 130, a cloud or other network 134, and/or a depth sensor or camera 136. Systems according to other embodiments of the present disclosure may comprise more or fewer components than the system 100. For example, the system 100 may not include one or more components of the computing device 102, the database 130, and/or the cloud 134.

The computing device 102 comprises a processor 104, a memory 106, a communication interface 108, and a user interface 110. Computing devices according to other embodiments of the present disclosure may comprise more or fewer components than the computing device 102.

The processor 104 of the computing device 102 may be any processor described herein or any similar processor. The processor 104 may be configured to execute instructions stored in the memory 106, which instructions may cause the processor 104 to carry out one or more computing steps utilizing or based on data received from the imaging device 112, the robot 114, the navigation system 118, the database 130, the cloud 134, and/or one or more components thereof.

The memory 106 may be or comprise RAM, DRAM, SDRAM, flash memory, other solid-state memory, any memory described herein, or any other tangible, non-transitory memory for storing computer-readable data and/or instructions. The memory 106 may store information or data useful for completing, for example, any step of the methods 300 and/or 400 described herein, or of any other methods. The memory 106 may store, for example, one or more gesture recognition algorithms 120, one or more image processing algorithms 122, one or more transformation algorithms 124, and/or one or more registration algorithms 128. Such instructions or algorithms may, in some embodiments, be organized into one or more applications, modules, packages, layers, or engines. The algorithms and/or instructions may cause the processor 104 to manipulate data stored in the memory 106 and/or received from or via the imaging device 112, the robot 114, the database 130, and/or the cloud 134. Additionally or alternatively, functionality provided by the various components of the memory 106 depicted and described herein can be provided by an artificial neural network or other type of machine learning model. Thus, while various components of the memory 106 are depicted as instructions, it should be appreciated that some or all of these components may be provided as an artificial neural network and may provide similar or the same functionality as the instructions described herein. In some embodiments, the computer-readable data may comprise the instructions and/or the machine learning models discussed herein (e.g., a neural network). For example, in embodiments where the system 100 comprises gesture-based data, the gesture-based data may be stored with the memory 106 and may, when processed (e.g., by the processor 104) may cause the processor to carry out any step of the method 300 and/or the method 400 discussed herein, or of any other method.

The computing device 102 may also comprise a communication interface 108. The communication interface 108 may be used for receiving image data or other information from an external source (such as the imaging device 112, the robot 114, the navigation system 118, the database 130, the cloud 134, and/or any other system or component not part of the system 100), and/or for transmitting instructions, images, or other information to an external system or device (e.g., another computing device 102, the imaging device 112, the robot 114, the navigation system 118, the database 130, the cloud 134, and/or any other system or component not part of the system 100). The communication interface 108 may comprise one or more wired interfaces (e.g., a USB port, an ethernet port, a Firewire port) and/or one or more wireless transceivers or interfaces (configured, for example, to transmit and/or receive information via one or more wireless communication protocols such as 802.11a/b/g/n, Bluetooth, NFC, ZigBee, and so forth). In some embodiments, the communication interface 108 may be useful for enabling the device 102 to communicate with one or more other processors 104 or computing devices 102, whether to reduce the time needed to accomplish a computing-intensive task or for any other reason.

The computing device 102 may also comprise one or more user interfaces 110. The user interface 110 may be or comprise a keyboard, mouse, trackball, monitor, television, screen, touchscreen, and/or any other device for receiving information from a user and/or for providing information to a user. The user interface 110 may be used, for example, to receive a user selection or other user input regarding any step of any method described herein. Notwithstanding the foregoing, any required input for any step of any method described herein may be generated automatically by the system 100 (e.g., by the processor 104 or another component of the system 100) or received by the system 100 from a source external to the system 100. In some embodiments, the user interface 110 may be useful to allow a surgeon or other user to modify instructions to be executed by the processor 104 according to one or more embodiments of the present disclosure, and/or to modify or adjust a setting of other information displayed on the user interface 110 or corresponding thereto.

Although the user interface 110 is shown as part of the computing device 102, in some embodiments, the computing device 102 may utilize a user interface 110 that is housed separately from one or more remaining components of the computing device 102. In some embodiments, the user interface 110 may be located proximate one or more other components of the computing device 102, while in other embodiments, the user interface 110 may be located remotely from one or more other components of the computer device 102.

The imaging device 112 may be operable to image anatomical feature(s) (e.g., a bone, veins, tissue, etc.) and/or other aspects of patient anatomy to yield image data (e.g., image data depicting or corresponding to a bone, veins, tissue, etc.). The imaging device 112 comprises an imaging source 113 and an imaging detector 115. "Image data" as used herein refers to the data generated or captured by an imaging device 112, including in a machine-readable form, a graphical/visual form, and in any other form. In various examples, the image data may comprise data corresponding to an anatomical feature of a patient, or to a portion thereof. The image data may be or comprise a preoperative image, an intraoperative image, a postoperative image, or an image taken independently of any surgical procedure. In some embodiments, a first imaging device 112 may be used to obtain first image data (e.g., a first image) at a first time, and a second imaging device 112 may be used to obtain second image data (e.g., a second image) at a second time after the first time. The imaging device 112 may be capable of taking a 2D image or a 3D image to yield the image data. The imaging device 112 may be or comprise, for example, an ultrasound scanner (which may comprise, for example, a physically separate transducer and receiver, or a single ultrasound transceiver), an O-arm, a C-arm, a G-arm, or any other device utilizing X-ray-based imaging (e.g., a fluoroscope, a CT scanner, or other X-ray machine), a magnetic resonance imaging (MRI) scanner, an optical coherence tomography (OCT) scanner, an endoscope, a microscope, an optical camera, a thermographic camera (e.g., an infrared camera), a radar system (which may comprise, for example, a transmitter, a receiver, a processor, and one or more antennae), or any other imaging device 112 suitable for obtaining images of an anatomical feature of a patient. The imaging device 112 may be contained entirely within a single housing, or may comprise a transmitter/emitter and a receiver/detector that are in separate housings or are otherwise physically separated.

In some embodiments, the imaging device 112 may comprise more than one imaging device 112. For example, a first imaging device may provide first image data and/or a first image, and a second imaging device may provide second image data and/or a second image. In still other embodiments, the same imaging device may be used to provide both the first image data and the second image data, and/or any other image data described herein. The imaging device 112 may be operable to generate a stream of image data. For example, the imaging device 112 may be configured to operate with an open shutter, or with a shutter that continuously alternates between open and shut so as to capture successive images. For purposes of the present disclosure, unless specified otherwise, image data may be considered to be continuous and/or provided as an image data stream if the image data represents two or more frames per second.

The imaging source 113 and the imaging detector 115 respectively generate and detect radiation, waves, or other signals for the purpose of generating one or more images. The imaging source 113 and the imaging detector 115 may generate different types of images (e.g., ultrasound images, x-ray images, etc.). In at least one embodiment, the imaging source 113 may generate x-rays, and the imaging detector 115 may detect the x-rays generated by the imaging source 113, such that any material or object therebetween is imaged. As previously noted, the imaging source 113 and imaging detector 115 may be in separate housings or otherwise physically separated, such that the imaging source 113 may be moved or repositioned relative to the imaging detector 115, and/or vice versa.

The robot 114 may be any surgical robot or surgical robotic system. The robot 114 may be or comprise, for example, the Mazor X™ Stealth Edition robotic guidance system. The robot 114 may be configured to position the imaging device 112, the imaging source 113, and/or the imaging detector 115 at one or more precise position(s) and orientation(s), and/or to return the imaging device 112, the imaging source 113, and/or the imaging detector 115 to the same position(s) and orientation(s) at a later point in time. The robot 114 may additionally or alternatively be configured to manipulate a surgical tool (whether based on guidance from the navigation system 118 or not) to accomplish or to assist with a surgical task. In some embodiments, the robot 114 may be configured to hold and/or manipulate an anatomical element during or in connection with a surgical procedure. The robot 114 may comprise one or more robotic arms 116. In some embodiments, the robotic arm 116 may comprise a first robotic arm and a second robotic arm, though the robot 114 may comprise more than two robotic arms. In some embodiments, one or more of the robotic arms 116 may be used to hold and/or maneuver the imaging device 112, the imaging source 113, and/or the imaging detector 115. In embodiments where the imaging device 112 comprises two or more physically separate components (e.g., the imaging source 113 and the imaging detector 115), one robotic arm 116 may hold one such component (e.g., the imaging source 113), and another robotic arm 116 may hold another such component (e.g., the imaging detector 115). Each robotic arm 116 may be positionable independently of the other robotic arm. The robotic arms may be controlled in a single, shared coordinate space, or in separate coordinate spaces.

The robot 114, together with the robotic arm 116, may have, for example, one, two, three, four, five, six, seven, or more degrees of freedom. Further, the robotic arm 116 may be positioned or positionable in any pose, plane, and/or focal point. The pose includes a position and an orientation. As a result, an imaging device 112 (or components thereof), surgical tool, or other object held by the robot 114 (or, more specifically, by the robotic arm 116) may be precisely positionable in one or more needed and specific positions and orientations.

The robotic arm(s) 116 may comprise one or more sensors that enable the processor 104 (or a processor of the robot 114) to determine a precise pose in space of the robotic arm (as well as any object or element held by or secured to the robotic arm).

In some embodiments, reference markers (i.e., navigation markers) may be placed on the robot 114 (including, e.g., on the robotic arm 116), the imaging device 112 (or components thereof), or any other object in the surgical space. The reference markers may be tracked by the navigation system 118, and the results of the tracking may be used by the robot 114 and/or by an operator of the system 100 or any component thereof. In some embodiments, the navigation system 118 can be used to track other components of the system (e.g., imaging device 112, imaging source 113, imaging detector 115) and the system can operate without the use of the robot 114 (e.g., with the surgeon manually manipulating the imaging device 112 and/or one or more surgical tools, based on information and/or instructions generated by the navigation system 118, for example).

The navigation system 118 may provide navigation for a surgeon and/or a surgical robot during an operation. The navigation system 118 may be any now-known or future-developed navigation system, including, for example, the Medtronic StealthStation™ S8 surgical navigation system or any successor thereof. The navigation system 118 may include one or more cameras or other sensor(s) for tracking one or more reference markers, navigated trackers, or other objects within the operating room or other room in which some or all of the system 100 is located. The one or more cameras may be optical cameras, infrared cameras, or other cameras. In some embodiments, the navigation system may comprise one or more electromagnetic sensors. In various embodiments, the navigation system 118 may be used to track a position and orientation (i.e., pose) of the imaging device 112, the robot 114 and/or robotic arm 116, and/or one or more surgical tools (or, more particularly, to track a pose of a navigated tracker attached, directly or indirectly, in fixed relation to the one or more of the foregoing). The navigation system 118 may include a display for displaying one or more images from an external source (e.g., the computing device 102, imaging device 112, or other source) or for displaying an image and/or video stream from the one or more cameras or other sensors of the navigation system 118. In some embodiments, the system 100 can operate without the use of the navigation system 118. The navigation system 118 may be configured to provide guidance to a surgeon or other user of the system 100 or a component thereof, to the robot 114, or to any other element of the system 100 regarding, for example, a pose of one or more anatomical elements, whether or not a tool is in the proper trajectory, and/or how to move a tool into the proper trajectory to carry out a surgical task according to a preoperative or other surgical plan.

The depth sensor 136 determines a working volume associated with the surgery or surgical procedure, performs dynamic collision avoidance, and/or facilitates gesture recognition (e.g., the depth sensor 136 may comprise one or more components of the computing device 102). The depth sensor 136 may determine the working volume based on a predetermined surgical plan (e.g., a surgical plan stored in the database 130), the position and/or orientation of one or more components of the system 100 (e.g., a volume around a surgical tool positioned proximate the surgical patient), the type or surgery or surgical procedure being conducted, combinations thereof, and/or the like. In some embodiments, the depth sensor 136 may determine (e.g., using or based on the results of one or more algorithms such as the registration algorithm 128) the movement or planned movement of one or more components of the system 100 (e.g., the imaging device 112 and/or components thereof, the robot 114, and/or the robotic arms 116) and prevent the one or more components from colliding. In some embodiments, the depth sensor 136 may be coupled with or be a part of the navigation system 118 and may assist with dynamic collision avoidance. In some embodiments, the depth sensor 136 may be a camera or other imaging system (e.g., LIDAR) capable of remotely sensing or determining ranges and/or depths of the working volume and the components of the system 100. In some embodiments, the depth sensor 136 may identify the anatomical features of the patient (e.g., the skeleton of the patient) to determine a working volume. For instance, the depth sensor 136 may identify that the patient is in a prone position and may identify the vertebrae of the spine (e.g., using one or more algorithms), and use the identification information to define the working volume as a volume including one or more vertebrae and an area above the patient (e.g., an area above the spine where a surgical tool may move or operate).

In at least one embodiment, the depth sensor 136 may identify one or more gestures associated with the surgeon, other individuals, or groups of individuals in the operating room or other room where the surgery or surgical procedure is taking place. For instance, the depth sensor 136 may capture movement or other physical actions taken by the individuals and send the captured movement information to components of the system 100 (e.g., the computing device 102). The depth sensor 136 may provide a continuous or live feed of captured gestures to the computing device 102, and the computing device 102 in turn may interpret or process the captured gestures to cause one or more actions in the system 100 (e.g., moving the imaging source 113 and the imaging detector 115 based on the gesture captured by the depth sensor 136). In some embodiments, the depth sensor 136 may implement gesture recognition software (e.g., OpenPose or other software capable of detecting human body and/or hand movements or gestures). The gesture recognition software may use, for example, pose estimation of various portions of the bodies of multiple individuals to determine the relative movements or gestures of the individuals.

As illustrated in FIG. 1B, a block diagram of data flow within the system 100 is illustrated. A surgeon 101 may perform a gesture 140. The gesture 140 may be the same as or similar to any gestured described herein. The gesture 140 may be seen, viewed, captured, or otherwise processed by the depth sensor 136. In some embodiments, the depth sensor 136 may capture a plurality of images/a live feed of the surgeon 101 performing the gesture 140. In some embodiments, additional or alternative components of the system 100 (e.g., the imaging device 112, the navigation system 118, etc.) may view, see, capture, or otherwise process the gesture 140. The image data produced by the depth sensor 136 may flow into the one or more image processing algorithms 122. The one or more image processing algorithms 122 may modify or otherwise adapt the image information (e.g., using Gaussian filters, edge detection, digital signal processing techniques, and/or the like) to produce processed data. The processed data may be sent to one or more gesture recognition algorithms 120. The one or more gesture recognition algorithms 120 may receive the processed data and identify one or more gestures (e.g., a gesture 140) performed by the surgeon 101. In some embodiments, the one or more gesture recognition algorithms 120 may use statistical classification (e.g., k-nearest neighbors algorithms, support vector machines (SVMs), etc.) to classify or identify the gesture 140. The one or more gesture recognition algorithms 120 may generate gesture data. The gesture data may be sent to and received by the computing device 102 and/or one or more components thereof (e.g., the processor 104). The gesture data may be used by the computing device 102 to control or otherwise cause movement in, for example, the imaging source 113, the robot 114, the imaging detector 115, and/or the robotic arms 116.

The system 100 or similar systems may be used, for example, to carry out one or more aspects of any of the methods 300 and/or 400 described herein. The system 100 or similar systems may also be used for other purposes.

Figure 2:
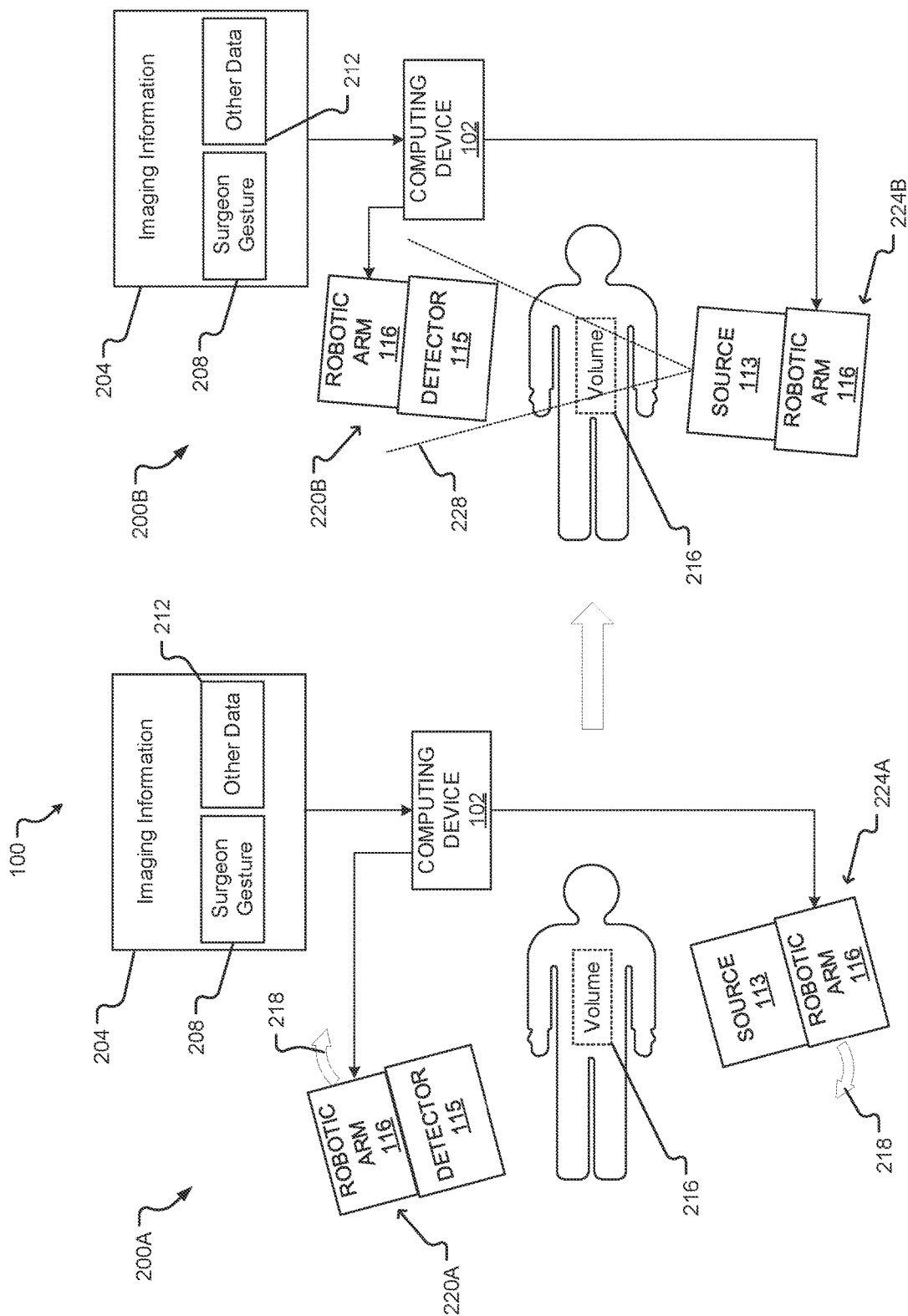
FIG. 2 illustrates a movement of the system according to at least one embodiment of the present disclosure.

FIG. 2 depicts a schematic of an implementation of the system 100 to perform a gesture-based surgical system according to at least one embodiment of the present disclosure. The components of the system 100 shown in FIG. 2 are in a first state 200A and one or more components such as the robotic arms 116 may move to create a second state 200B based on, for example, one or more gestures (e.g., gestures performed by a surgeon).

The system 100 comprises a computing device 102, an imaging source 113, an imaging detector 115, and robotic arms 116. The imaging source 113 and the imaging detector 115 are respectively attached to the robotic arms 116. The computing device 102 receives imaging information 204 (e.g., image data or other image information captured from imaging devices such as an imaging device 112), as well as a surgeon gesture 208 and/or other data 212 and causes the imaging source 113 and imaging detector 115 to change pose (i.e., position and/or orientation) based on the received information through, for example, the movement of respective robotic arms 116. In both the first state 200A and the second state 200B, a working volume 216 is defined by the system 100. The working volume 216 is a two-dimensional (2D) or three-dimension (3D) volume defining an area of operation for the surgery or surgical procedure. While in the first state 200A, the imaging source 113 and the detector 115 are not aligned relative to the working volume 216 and are thus unable to capture images of the entirety of the working volume 216. The first state 200A may exist, for example, before a surgery is performed, or intraoperative or postoperatively when image capturing of the working volume 216 is not required. In some embodiments, the first state 200A may be or represent a transitional phase between two fixed states where one or more of the imaging source 113 and the imaging detector 115 are moving relative to the working volume 216 and are unable to capture images. However, once the system 100 enters the second state 200B, the imaging source 113 and the imaging detector 115 are aligned with one another in relation to the working volume 216, and an image of the working volume 216 is able to be captured. More specifically, the imaging source 113 is configured to emit radiation, waves, or other signals in an area 228 that are captured or received at the imaging detector 115 to generate an image of the working volume 216 located within the area 228. In some embodiments, when in the second state 200B the imaging source 113 and the imaging detector 115 may be fixed or static relative to one another, relative to the working volume 216, and/or relative to one or more other components of the system 100.

The surgeon gesture 208 is a predetermined movement by the surgeon that is recognized by the computing device 102 (e.g., using one or more algorithms and/or one or more machine learning or artificial intelligence systems) and is used by the computing device 102 to position one or more components of the system 100 (e.g., the imaging source 113 and the imaging detector 115). The surgeon gesture 208 may be a hand gesture (e.g., pointing with a finger, closing a hand, rotating and/or translating the hand, etc.), an arm gesture (e.g., a raising or lowering of an arm, a movement of the arm from a first position to a second position, etc.), and/or an eye gesture (e.g., blinking, closing one or both eyes, looking at a certain location for a predetermined amount of time, etc.). In some embodiments, additional or alternative surgeon gestures may be recognized by the system 100, and the examples listed here are in no way limiting.

The other data 212 may be a gesture made by another individual in the room or operating room in which the surgery or surgical procedure takes place or may another form of verbal or non-verbal communication (e.g., the surgeon says "take picture" which causes the imaging source 113 and the imaging detector 115 to capture a picture at their current pose) capable of being interpreted by the computing device 102. The computing device 102 may implement one or more algorithms (e.g., a gesture recognition algorithm 120, an image processing algorithm 122, etc.) to identify the surgeon gesture 208, and move the imaging source 113 and the imaging detector 115 based thereon. For example, the surgeon gesture 208 may be a hand gesture (e.g., a finger pointing to the working volume) by made by the surgeon. In this example, the computing device 102 and/or components thereof (e.g., the depth sensor 136) may receive the imaging information 204 comprising the surgeon gesture 208 (e.g., the imaging information 204 may comprise a live feed that captures the surgeon performing the surgeon gesture 208). In some embodiments, the computing device 102 may cause different actions or movement of components of the system 100 based on the type, speed, and/or number of gestures associated with the surgeon gesture 208 and/or the other data 212.

In some embodiments, the surgeon gesture 208 and/or the other data 212 may generate secondary information, and the system 100 and/or components thereof (e.g., the computing device 102) may utilize the secondary information in addition to or alternatively to the surgeon gesture 208 and/or the other data 212 to maneuver the imaging source 113 and the imaging detector 115 relative to the working volume 216, or alternatively relative to the patient, the surgeon, combinations thereof, and the like. For instance, the secondary information may be a silhouette formed one an anatomical object (e.g., a vertebra, a rib, etc.) by a hand gesture made by the surgeon. The computing device 102 may receive (e.g., from the depth sensor 136, the navigation system 118, and/or the imaging device 112) information pertaining to the location and/or orientation the silhouette with respect to the working volume 216 and cause the imaging source 113 and the imaging detector 115 to move relative to the silhouette and/or the working volume 216 based on the information about the silhouette.

In some embodiments, the surgeon gesture 208 and/or the other data 212 may cause the movement or operation of additional or alternative components of the system 100 (e.g., the robotic arms 116, a surgical tool, etc.). In some embodiments, a first set of gestures of the surgeon gesture 208 and/or the other data 212 (e.g., a hand gesture with a pointed finger, an arm motion, two hands in a particular pose, etc.) may cause a first set of actions of the components of the system 100 (e.g., move a surgical tool to a first location) and a second set of gestures of the surgeon gesture 208 and/or the other data 212 (e.g., a hand gesture in the form of a fist) may cause a second set of actions of the components of the system 100 (e.g., causing a surgical tool to drill, cut, ream, etc. anatomical tissue). In some embodiments, the surgeon gesture 208 and/or the other data 212 may be or comprise a series or plurality of gestures. For example, the surgeon gesture 208 may be multiple gestures (e.g., multiple hand gestures in the form of pointing) at different areas in the working volume to define a sub-working volume that is then imaged by the imaging source 113 and the imaging detector 115. In such embodiments, the depth sensor 136 may capture the multiple hand gestures and determine (e.g., using the gesture recognition algorithm 120) the sub-volume and cause the imaging source 113 and the imaging detector 115 to image the sub-volume. In at least one embodiment, the hand gestures may be two pointing gestures that serve as endpoints with any space in the working volume that falls on a straight imaginary line connecting the two endpoints being imaged. The gestures, for example, may be made on either side of an anatomical element the surgeon wishes to image (e.g., a vertebra, a rib, etc.) and the depth sensor 136 may identify the anatomical element as falling on the straight imaginary line connecting the two points in space and image the anatomical element.

In some embodiments, the surgeon gesture 208 and/or the other data 212 may be used by the system 100 to fine tune the pose of the imaging source 113 and the imaging detector 115. For instance, the imaging source 113 and the imaging detector 115 may be positioned proximate to the working volume 216 based on, for example, a surgical plan. The surgeon may instruct the system 100 to capture an image (e.g., using the surgeon gesture 208) and the computing device 102 may render the captured image to a user interface (e.g., a user interface 110) so the surgeon can review the image. The surgeon may determine that the image is unclear, inaccurate, or is otherwise insufficient for the purposes of the surgery or surgical procedure and provide the surgeon gesture 208 and/or the other data 212 to fine tune the pose of the imaging source 113 and the imaging detector 115 to capture an improved image. The fine tuning may comprise the computing device 102 causing the imaging source 113 and the imaging detector 115 to move in a predetermined pattern and/or to capture a plurality of images, with each image captured after the imaging source 113 and the imaging detector 115 are moved to a plurality of different poses. The plurality of images may then be rendered to the user interface, and the surgeon may use a preferred image for the purposes of the surgery or surgical procedure. In some embodiments, the imaging source 113 and the imaging detector 115 may provide a live feed rendered to the user interface, which may allow the surgeon to fine tune the positioning of the imaging source 113 and/or the imaging detector 115 using the surgeon gesture 208 and/or the other data 212. Once the surgeon has oriented the imaging source 113 and the imaging detector 115 to a location that provides the optimal image (which may be based on the live feed), the surgeon may provide the surgeon gesture 208 and/or the other data 212 to instruct the system 100 to capture an image.

In some embodiments, the surgeon gesture 208 and/or the other data 212 may be used by the system 100 and/or components thereof (e.g., the computing device 102) to move one or more components of the system 100 (e.g., the imaging source 113 and the imaging detector 115) along a direction indicated by the gesture. The surgeon gesture 208 and/or the other data 212 may define a direction (e.g., a direction in which a finger points in a hand gesture, a direction a surgeon is looking in an eye gesture, etc.) and the system 100 may identify (e.g., using one or more algorithms such as the gesture recognition algorithm 120) the direction and cause the imaging source 113 and the imaging detector 115 to move in relation to the direction. For example, the surgeon may use the surgeon gesture 208 and/or the other data 212 to define a first direction, and the system 100 may cause the imaging source 113 to move in the first direction (and cause the imaging detector 115 to move in a complementary direction such that the imaging source 113 and the imaging detector 115 can still capture an image of the working volume 216 once the imaging source 113 has moved in the first direction). In some embodiments, the movement in the first direction may be based on the type, speed, and/or duration of the gesture. As in the previous example, a hand gesture in the form of a finger pointing in the first direction may cause the imaging source 113 to move in the first direction until the surgeon stops performing the hand gesture.

In some embodiments, the surgeon gesture 208 may be or comprise gestures corresponding to a plurality of motions (e.g., the surgeon moves his arm from one side of a patient to another side of the patient, the surgeon twirls his arm in a circle, the surgeon moves his hand up to indicate a stop motion, etc.) that may be captured by one or more components of the system 100 (e.g., the imaging device 112, the navigation system 118, the depth sensor 136, etc.). In such embodiments, the surgeon gesture 208 may be captured in a video or one or more sequences of images. The captured video or sequences of images may be processed (e.g., using one or more gesture recognition algorithms 120 and/or one or more image processing algorithms 122) to determine the surgeon gesture 208.

In some embodiments, the surgeon gesture 208 and/or the other data 212 may cause the system 100 to verify one or more aspects of the surgery or surgical procedure. Non-limiting aspects include verifying the position of the working volume 216, the position of anatomical elements in the working volume 216 (e.g., positions of ribs, vertebrae, etc.), the position of other objects in the working volume 216 (e.g., surgical tools, minimally invasive surgery (MIS) towers, screws embedded in anatomical elements, etc.). In some embodiments, the system 100 may verify the aspects using one or more algorithms (e.g., the image processing algorithms 112, the transformation algorithms 124, the registration algorithms 128, etc.). In at least one embodiment, the system 100 may verify the accuracy of object locations within the working volume 216 using the transformation algorithm 124, which may compare data associated an image captured by the imaging source 113 and the imaging detector 115 with data provided by the depth sensor 136 to confirm the accuracy of the determined locations of the object within the working volume 216.

Figure 3:
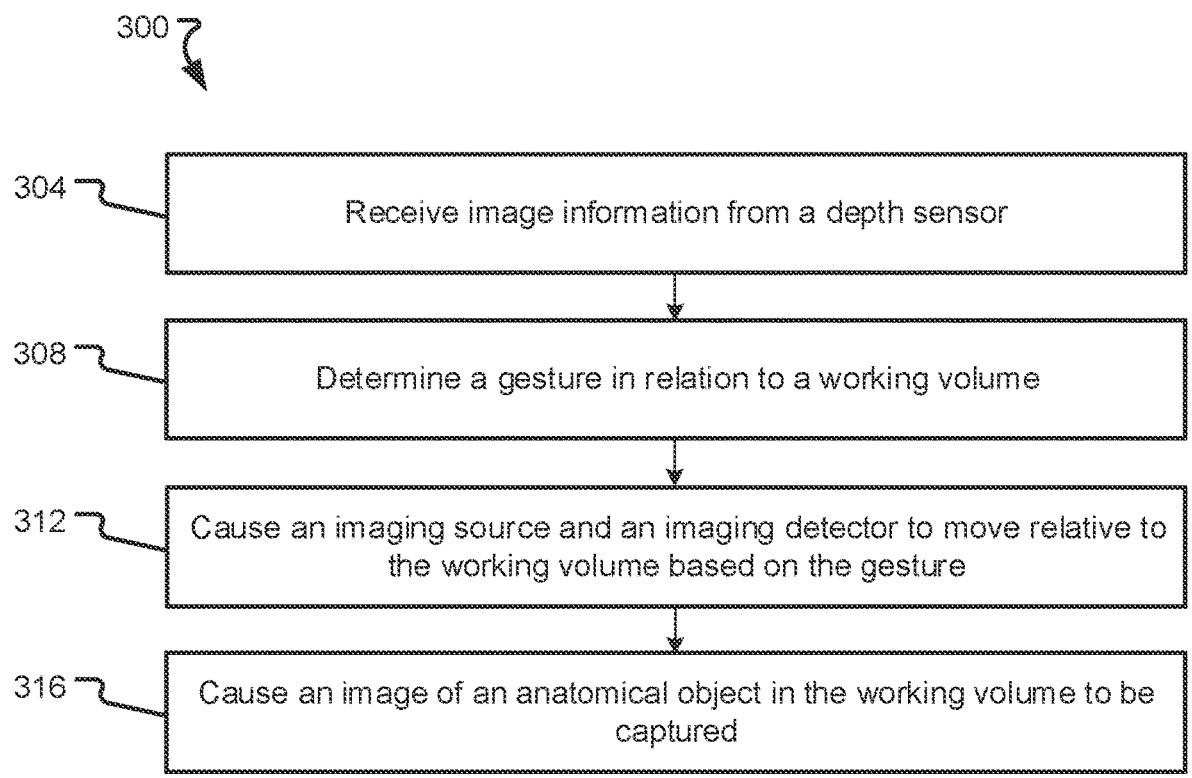
FIG. 3 is a flowchart illustrating a method for gesture-based positioning of imaging devices according to at least one embodiment of the present disclosure.

FIG. 3 depicts a method 300 that may be used, for example, to cause imaging components to be moved relative to a working volume and capture an image using gesture-based commands.

The method 300 (and/or one or more steps thereof) may be carried out or otherwise performed, for example, by at least one processor. The at least one processor may be the same as or similar to the processor(s) 104 of the computing device 102 described above. The at least one processor may be part of a robot (such as a robot 114) or part of a navigation system (such as a navigation system 118). A processor other than any processor described herein may also be used to execute the method 300. The at least one processor may perform the method 300 by executing instructions stored in a memory such as the memory 106. The instructions may correspond to one or more steps of the method 300 described below. The instructions may cause the processor to execute one or more algorithms, such as a gesture recognition algorithm 120, an image processing algorithm 122, a transformation algorithm 124, and/or a registration algorithm 128.

The method 300 comprises receiving image information from a depth sensor (step 304). The image information may comprise information about poses of various elements of a system (e.g., a system 100), such as the poses of an imaging source (e.g., an imaging source 113) and an imaging detector (e.g., an imaging detector 115). The depth sensor (e.g., a depth sensor 136) determines a working volume (e.g., a working volume 216) associated with a surgery or surgical procedure and identifies one or more objects located therein (e.g., surgical tools, anatomical elements, etc.). The depth sensor may determine the working volume based on, for example, a surgical plan, the pose of one or more components proximate a patient (e.g., surgical tools), the type of surgery performed, and the like. The image information generated from or otherwise captured and forwarded by the depth sensor may be received by one or more processing components (e.g., the processor and/or a computing device 102). In some embodiments, the information may additionally or alternatively be stored or saved in a database (e.g., in a database 130). In at least one embodiment, the image information may comprise information about or relating to at least one gesture (e.g., a surgeon gesture or other data).

The method 300 also comprises determining a gesture in relation to a working volume (step 308). The gesture may be a surgeon gesture such as a surgeon gesture 208 and/or other data such as other data 212 in relation to a working volume such as a working volume 216. In some embodiments, the step 308 may utilize a gesture recognition algorithm (e.g., a gesture recognition algorithm 120) to process the received image information and determine one or more gestures therefrom. In some embodiments, the gesture recognition algorithm may identify the pose or location of the gesture relative to the working volume (e.g., within the working volume, outside the working volume, etc.). Depending on the definition of the working volume, the gesture recognition algorithm may identify that the gesture is directed toward one or more elements inside the working volume (e.g., patient anatomy, surgical tools or other surgical objects, imaging elements such as the imaging source and the imaging detector, etc.). For example, the gesture recognition algorithm may identify that the gesture is directed toward an anatomical element (e.g., a rib) and/or one or more surgical instruments proximate thereto (e.g., a screw, an MIS tower, etc.).

The method 300 also comprises causing an imaging source and an imaging detector to move relative to the working volume based on the gesture (step 312). The imaging source and imaging detector may be attached to respective robotic arms (e.g., robotic arms 116), and may be moved by the movement of the robotic arms. In some embodiments, the method 300 may use the determined gesture to perform a predetermined movement. For instance, the identified gesture may indicate that the surgeon wishes to capture an image of one or more portions of the working volume (e.g., the gesture may be a hand gesture pointing toward an anatomical element in the working volume the surgeon wishes to image). The robotic arms (and subsequently the imaging source and imaging detector) may then be caused to move from a first position to a second position (e.g., from a position in which capturing the image is infeasible into a position where the image can be captured).

In some embodiments, information about the current location of the robotic arms may be received by the processor, and the movement of the imaging source and imaging detector may be monitored by the depth sensor. In instances where the depth sensor detects that the movement of the robotic arms may create a collision, the depth sensor may provide such information to the processor, which may reroute the imaging source and the imaging detector to avoid a collision. In some embodiments, the movement of the imaging source and the imaging detector may be predetermined based on information generated by the depth sensor (e.g., the existing location of elements in the operating room) to prevent collisions.

The method 300 also comprises causing an image of an anatomical object in the working volume to be captured (step 316). The anatomical object may be a vertebra, rib, or other anatomical element identified by the gesture and the imaging source and imaging detector may emit and detect respectively radiation, waves, or other signals to image the anatomical object (e.g., x-ray radiation, ultrasound waves, etc.). In some embodiments, an additional gesture may be provided by the surgeon and recognized and processed by the system to cause the image to be captured. For example, the surgeon may provide a first hand gesture (e.g., a finger pointing at the anatomical object) to signal the system to move the imaging source and imaging detector, and a second hand gesture (e.g., closing the hand to form a fist) to signal to the system to capture the anatomical object in the working volume. In some embodiments, the captured image may be rendered to a user interface.

The present disclosure encompasses embodiments of the method 300 that comprise more or fewer steps than those described above, and/or one or more steps that are different than the steps described above.

Figure 4:
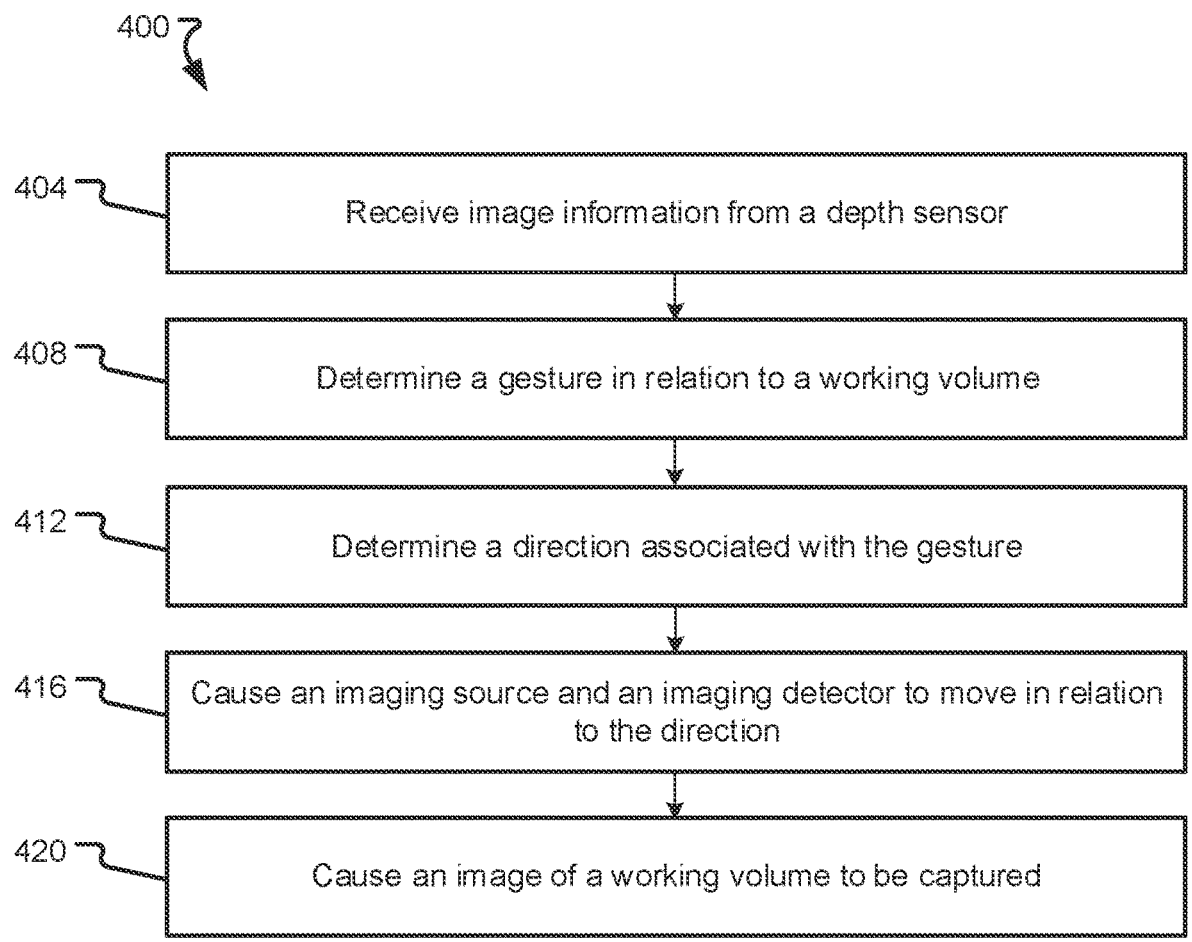
FIG. 4 is a flowchart illustrating a method for positioning of imaging devices based on a gesture direction according to at least one embodiment of the present disclosure.

FIG. 4 depicts a method 400 that may be used, for example, to cause imaging components to be moved relative to a working volume based on a direction associated with a gesture.

The method 400 (and/or one or more steps thereof) may be carried out or otherwise performed, for example, by at least one processor. The at least one processor may be the same as or similar to the processor(s) 104 of the computing device 102 described above. The at least one processor may be part of a robot (such as a robot 114) or part of a navigation system (such as a navigation system 118). A processor other than any processor described herein may also be used to execute the method 400. The at least one processor may perform the method 400 by executing instructions stored in a memory such as the memory 106. The instructions may correspond to one or more steps of the method 400 described below. The instructions may cause the processor to execute one or more algorithms, such as a gesture recognition algorithm 120, an image processing algorithm 122, a transformation algorithm 124, and/or a registration algorithm 128.

The method 400 comprises receiving image information from a depth sensor (step 404). In some embodiments, the step 404 may be similar to or the same as the step 304 of the method 300. In some embodiments, the image information may be captured or generated by a depth sensor (e.g., a depth sensor 136) and may be passed to a system (e.g., a system 100) and/or one or more components thereof (e.g., a computing device such as a computing device 102).

The method 400 also comprises determining a gesture in relation to a working volume (step 408). In some embodiments, the step 408 may be similar to or the same as the step 308 of the method 300. In some embodiments, the gesture may be directed toward an anatomical element (e.g., a vertebra, a rib, etc.), and the method 400 may utilize a gesture recognition algorithm (e.g., a gesture recognition algorithm 120) to identify the location and type of gesture provided.

The method 400 also comprises determining a direction associated with the gesture (step 412). The processor may utilize the gesture recognition algorithm to determine the direction associated with the gesture (e.g., the direction in which a hand gesture, the direction of the gaze of a surgeon's eyes, the direction in which the surgeon's body is oriented, etc.). In some embodiments, the gesture recognition algorithm may determine the pose or location of the gesture relative to the working volume (e.g., an entry angle of the gesture into the working volume, whether the gesture occurs inside the working volume or outside the working volume, etc.). In at least one embodiment, the processor may identify one or more trajectories of the gesture and/or define imaginary lines representing the one or more trajectories. For example, the processor may identify the gesture as a hand gesture pointing in a first direction. The processor may, based on the first direction, define one or more trajectories along which the components of the system (e.g., movement of the robotic arms, movement of a surgical tool) may move. The processor may additional or alternatively create one or more imaginary lines to represent the one or more trajectories. In some embodiments, the imaginary lines and/or the one or more trajectories may be rendered to the user interface.

The method 400 also comprises causing an imaging source and an imaging detector to move in relation to the direction (step 416). In some embodiments, the imaging source or the imaging detector may move in the direction, while the other may move in a complementary fashion to ensure an image can be captured. For instance, if the gesture were interpreted by the system to be in a first direction, the robotic arm connected to the imaging source may be caused to move in the first direction, while the complementary robotic arm connected to the imaging detector may move in a second direction such that an image of the working volume can be captured after the imaging source stops moving in the first direction. In some embodiments, the gesture may cause the system to align the imaging source and imaging detector along one of the imaginary lines.

As an example, the surgeon may wish to image an anatomical element (e.g., a vertebra) and may provide a plurality of gestures (e.g., a plurality of hand gestures) all pointing at the anatomical element various angles. The system may then determine the hand gestures as well as the directions associated therewith (as noted respectively in the steps 412 and 416) and generate a plurality of trajectories associated with the directions. The system may then cause the imaging source and imaging detector to move such that both components are aligned along the trajectory, and may capture images of each angle (e.g., the imaging source and imaging detector are aligned along a first trajectory and capture a first image, then are moved such that the two components align along a second trajectory and capture a second image, etc.).

The method 400 also comprises cause an image of a working volume to be captured (step 420). In some embodiments, the step 416 may be similar to or the same as the step 312 of the method 300. In some embodiments, the entirety of the working volume may be captured, while in other embodiments one or more portions or sub-volumes of the working volume may be captured. In some embodiments, the gesture determined by the system (such as in the step 408) may indicate the number of images to capture and/or the angles at which the images should be captured. For instance, the surgeon may provide a hand gesture with a certain number of fingers extended (e.g., one finger, two fingers, three fingers, four fingers, etc.) which may correspond to the number of images captured. In at least one embodiment, the imaging source and imaging detector may be aligned along an imaginary line (e.g., the imaging source at one end of the imaginary line and the imaging detector at the other end of the imaginary line) such that the image captured may be of the working volume defined between the two endpoints.

The present disclosure encompasses embodiments of the method 400 that comprise more or fewer steps than those described above, and/or one or more steps that are different than the steps described above.

As noted above, the present disclosure encompasses methods with fewer than all of the steps identified in FIGS. 3 and 4 (and the corresponding description of the methods 300 and 400), as well as methods that include additional steps beyond those identified in FIGS. 3 and 4 (and the corresponding description of the methods 300 and 400). The present disclosure also encompasses methods that comprise one or more steps from one method described herein, and one or more steps from another method described herein. Any correlation described herein may be or comprise a registration or any other correlation.

The foregoing is not intended to limit the disclosure to the form or forms disclosed herein. In the foregoing Detailed Description, for example, various features of the disclosure are grouped together in one or more aspects, embodiments, and/or configurations for the purpose of streamlining the disclosure. The features of the aspects, embodiments, and/or configurations of the disclosure may be combined in alternate aspects, embodiments, and/or configurations other than those discussed above. This method of disclosure is not to be interpreted as reflecting an intention that the claims require more features than are expressly recited in each claim. Rather, as the following claims reflect, inventive aspects lie in less than all features of a single foregoing disclosed aspect, embodiment, and/or configuration. Thus, the following claims are hereby incorporated into this Detailed Description, with each claim standing on its own as a separate preferred embodiment of the disclosure.

Moreover, though the foregoing has included description of one or more aspects, embodiments, and/or configurations and certain variations and modifications, other variations, combinations, and modifications are within the scope of the disclosure, e.g., as may be within the skill and knowledge of those in the art, after understanding the present disclosure. It is intended to obtain rights which include alternative aspects, embodiments, and/or configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A system comprising:
an imaging source;
an imaging detector separate from the imaging source;
a depth sensor; and
a controller,
wherein the controller receives image information from the depth sensor, determines a gesture in relation to a working volume, and moves the imaging source and the imaging detector relative to the working volume based on the gesture, and wherein the imaging source is moved in a complementary motion relative to the imaging detector such that the imaging source is substantially aligned with the imaging detector after the imaging source and the imaging detector have been moved.

2. The system of claim 1, wherein the gesture is performed by a surgeon.

3. The system of claim 1, wherein the gesture comprises a hand gesture.

4. The system of claim 1, wherein the controller determines the gesture based on a silhouette formed on an anatomical element by the gesture.

5. The system of claim 1, wherein the controller determines a direction associated with the gesture and causes the imaging source and the imaging detector to move in relation to the direction.

6. The system of claim 1, wherein the imaging source is moved with a first robotic arm, and wherein the imaging detector is moved with a second robotic arm.

7. The system of claim 1, wherein the controller causes the imaging source and the imaging detector to capture an image of an anatomical object in the working volume, and wherein the controller causes the image to be rendered to a user interface.

8. The system of claim 7, wherein the anatomical object is a vertebra.

9. The system of claim 7, wherein the anatomical object is a rib.

10. A system comprising:
a processor; and
a memory storing data for processing by the processor that, when processed by the processor, cause the processor to:
receive image information from a depth sensor;
determine a gesture in relation to a working volume;
cause an imaging source and an imaging detector housed separately from the imaging source to move relative to the working volume based on the gesture, wherein the imaging source moves in a complementary motion relative to the imaging detector such that the imaging source and the imaging detector are aligned after the imaging source and the imaging detector have moved relative to the working volume; and cause an image of an anatomical object in the working volume to be captured.

11. The system of claim 10, wherein the gesture is performed by an individual in an operating room.

12. The system of claim 10, wherein the gesture is at least one of a hand gesture, an arm gesture, and an eye gesture.

13. The system of claim 10, wherein the processor determines the gesture based on a silhouette formed on the anatomical object by the gesture.

14. The system of claim 10, wherein the data further causes the processor to:
cause a surgical tool to move relative to the working volume based on the gesture.

15. The system of claim 10, wherein the anatomical object comprises at least one of a vertebra and a rib.

16. The system of claim 10, wherein the working volume is determined based on a surgical plan.

17. The system of claim 10, wherein the working volume contains a screw, and wherein the data further causes the processor to verify a position of the screw based on the gesture.

18. The system of claim 10, wherein the data further cause the processor to:
render, to a user interface, the image of the anatomical object.

19. A method comprising:
receiving image information from a depth sensor;
determining a gesture in relation to a working volume;
causing an imaging source and an imaging detector physically separated from the imaging source to move relative to the working volume based on the gesture, wherein the imaging source is moved in a complementary motion relative to the imaging detector such that the imaging source is substantially aligned with the imaging detector after the imaging source and the imaging detector have been moved; and
causing an image of an anatomical object in the working volume to be captured with the imaging detector.

20. The method of claim 19, further comprising:
determining a direction associated with the gesture; and
causing the imaging source and the imaging detector to move in relation to the direction associated with the gesture.

* * * * *